(12) United States Patent
Sablone et al.

(10) Patent No.: US 10,881,554 B2
(45) Date of Patent: Jan. 5, 2021

(54) METHOD AND APPARATUS FOR PRODUCING ABSORBENT SANITARY ARTICLES

(71) Applicant: Fameccanica.Data S.p.A., San Giovanni Teatino (IT)

(72) Inventors: Gabriele Sablone, Pescara (IT); Oscar Centorame, Giulianova (IT)

(73) Assignee: FAMECCANICA.DATA S.P.A., San Giovanni Teatino (IT)

(*) Notice: Subject to any disclaimer, the term of this patent is extended or adjusted under 35 U.S.C. 154(b) by 0 days.

(21) Appl. No.: 16/218,276

(22) Filed: Dec. 12, 2018

(65) Prior Publication Data

US 2019/0175422 A1   Jun. 13, 2019

(30) Foreign Application Priority Data

Dec. 13, 2017   (IT) .................. 102017000143770

(51) Int. Cl.
| | |
|---|---|
| *A61F 13/15* | (2006.01) |
| *A61F 13/493* | (2006.01) |
| *A61F 13/49* | (2006.01) |
| *A61F 13/496* | (2006.01) |

(52) U.S. Cl.
CPC .. *A61F 13/15699* (2013.01); *A61F 13/15723* (2013.01); *A61F 13/15739* (2013.01); *A61F 13/15747* (2013.01); *A61F 13/15804* (2013.01); *A61F 13/4902* (2013.01); *A61F 13/493* (2013.01); *A61F 13/496* (2013.01)

(58) Field of Classification Search
None
See application file for complete search history.

(56) References Cited

U.S. PATENT DOCUMENTS

| 6,447,628 B1 | 9/2002 | Couillard et al. |
| 2015/0173957 A1 | 6/2015 | Schneider et al. |
| 2016/0250082 A1* | 9/2016 | Hamamoto ......... A61F 13/4963 2/400 |

FOREIGN PATENT DOCUMENTS

| EP | 1013251 A1 | 6/2000 |
| WO | 2012087705 A1 | 6/2012 |

OTHER PUBLICATIONS

Italian Search Report and Written Opinion dated Aug. 15, 2018 for Italian Application No. IT201700143770.

\* cited by examiner

*Primary Examiner* — Barbara J Musser
(74) *Attorney, Agent, or Firm* — Patterson + Sheridan, LLP

(57) ABSTRACT

A method for producing absorbent sanitary articles, including: advancing in a machine direction a continuous composite tape comprising a first elastic band and a second elastic band, folding said continuous composite tape around a longitudinal axis parallel to the machine direction, cutting second connection zones of the second elastic band with two cuts spaced apart from each other, removing scrap portions of the second elastic band between said cuts, cutting first connection zones of the first elastic band, and folding in opposite directions portions of the first connection zone and overlapping end edges of the first connection zone to corresponding end edges of the second connection zone.

12 Claims, 14 Drawing Sheets

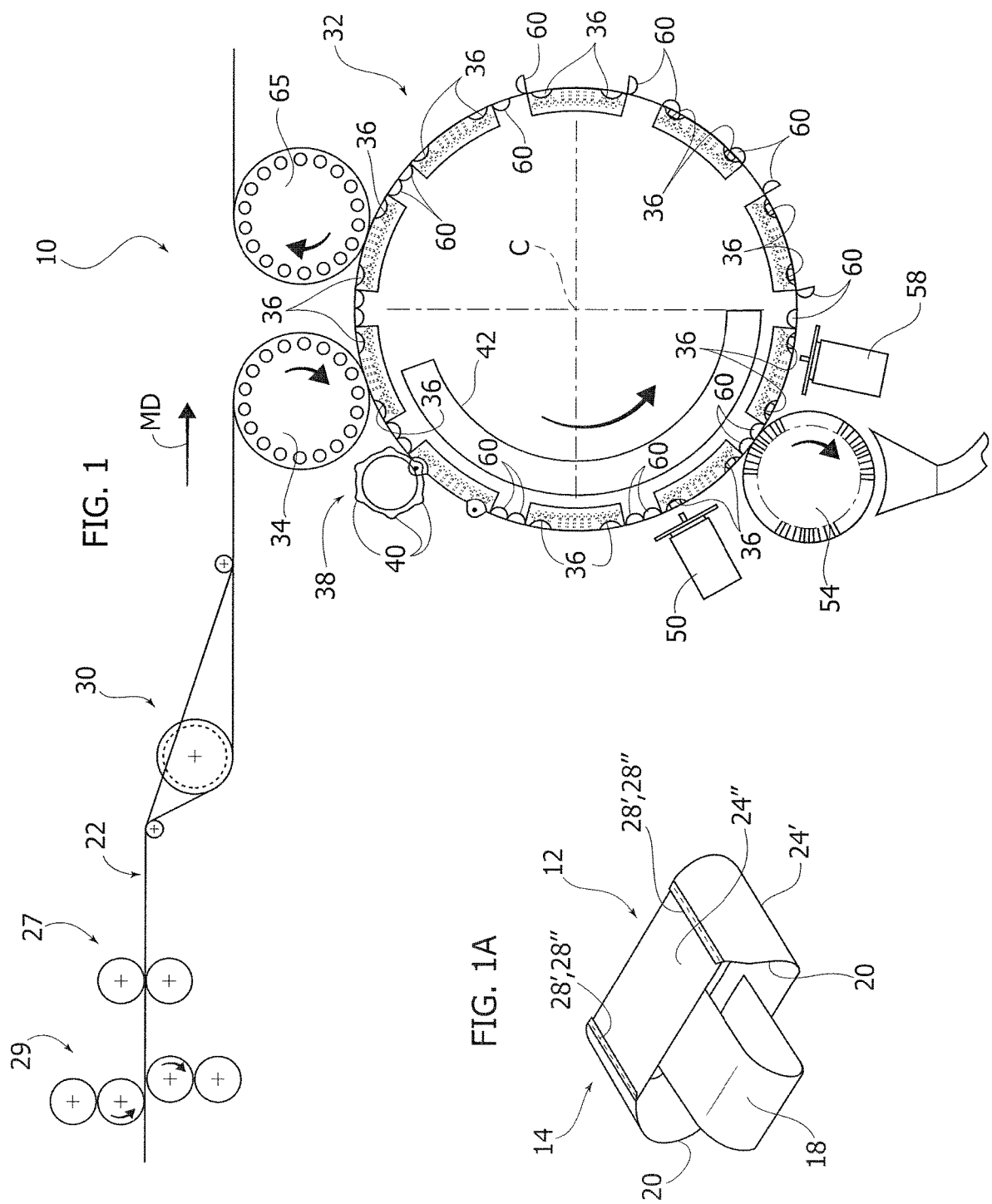

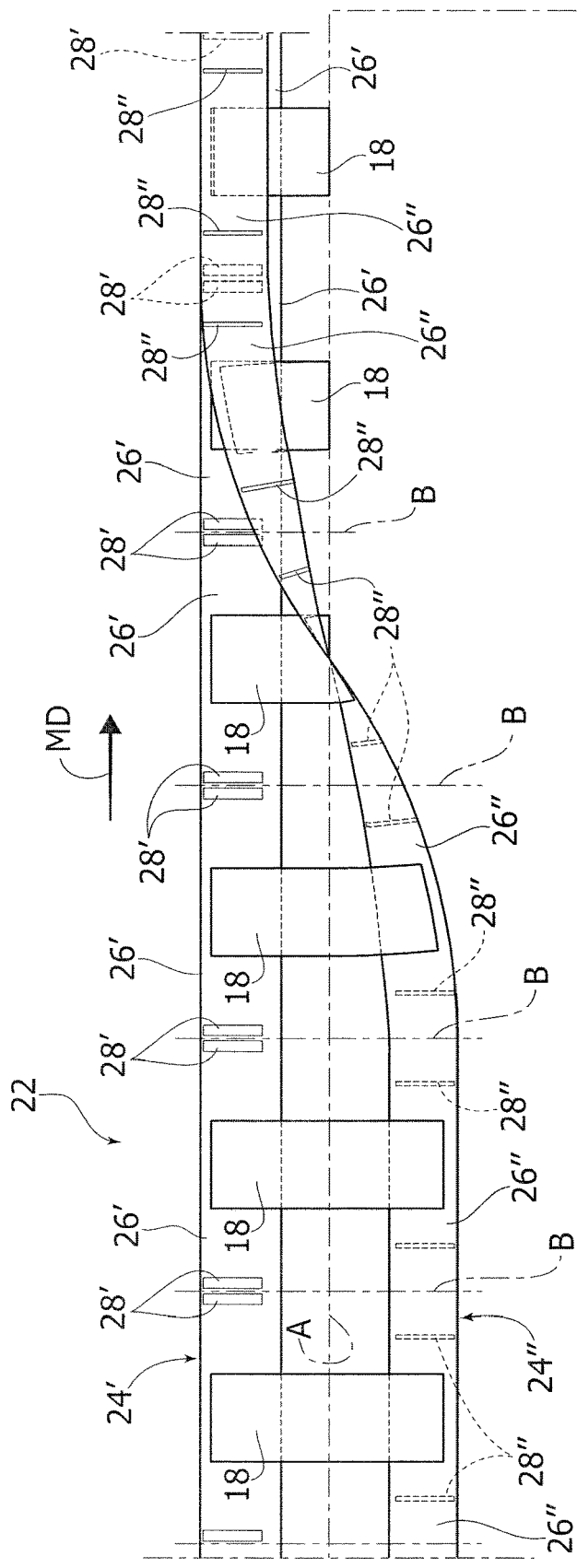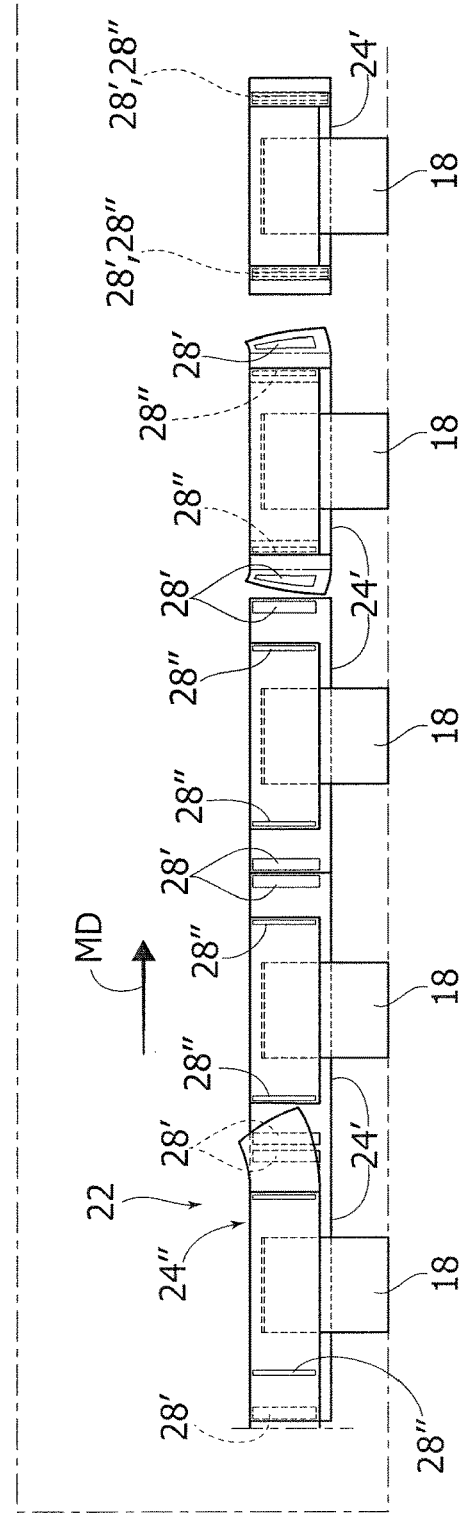

METHOD AND APPARATUS FOR PRODUCING ABSORBENT SANITARY ARTICLES

CROSS-REFERENCE TO RELATED APPLICATIONS

This application claims benefit of Italian patent application number 102017000143770, filed Dec. 13, 2017 which is herein incorporated by reference.

BACKGROUND OF THE INVENTION

Field of the Invention

The present invention relates to a method and an apparatus for producing absorbent sanitary articles.

The invention has been developed in particular for producing absorbent sanitary articles wearable as pants, for example the so-called training pants. The invention is applicable both for producing absorbent sanitary articles of the permanently sealed type and of the resealable type.

The present invention relates in particular to a method and an apparatus for producing absorbent sanitary articles according to the production technique normally called "Cross Direction".

Description of Prior Art

One consolidated technique for producing absorbent sanitary articles wearable as pants (of the permanently sealed or resealable type) consists of forming a continuous composite tape movable in a machine direction and formed by a continuous chain of product blanks which are positioned with the longitudinal axis of each individual article transversal with respect to the machine direction. This production technique is normally called "Cross Direction" and differs from the more traditional production technique called "Machine Direction" which involves producing the absorbent sanitary articles while they advance with their longitudinal axis parallel to the machine direction.

Examples of methods for producing absorbent sanitary articles according to the Cross Direction technique are described in documents EP-A-1013251, IT1379452, IT1410464 and IT1410465 by the same Applicant.

The continuous composite tape forming the chain of product blanks may comprise two elastic bands which are parallel to the machine direction and spaced apart from each other in a direction orthogonal to the machine direction, and a plurality of absorbent cores which extend between the two elastic bands orthogonally to the machine direction. The continuous composite tape advancing in the machine direction is folded along a longitudinal axis parallel to the machine direction, so that said elastic bands overlap onto each other.

For producing absorbent sanitary articles which are permanently sealed in the form of pants the continuous composite tape, after being folded longitudinally, is subjected to a welding step which creates transversal welds between the two elastic bands along weld lines which are spaced apart from each other in the machine direction by a predetermined pitch.

For producing absorbent sanitary articles which are openable and resealable, openable and resealable closing elements are applied on the continuous composite tape which are coupled to each other after the longitudinal folding of the continuous composite tape.

In traditional methods for producing absorbent sanitary articles according to the Cross Direction technique, the sealing of the absorbent sanitary articles (which may be formed by welds or by openable and resealable closing elements) is usually located on the sides of the waistbands of the absorbent sanitary articles.

The presence of welds or openable and resealable closing elements on the sides of the absorbent sanitary articles may be unwanted. Some producers of absorbent sanitary articles may prefer the production of absorbent sanitary articles in which the sealing zones of the waistbands are positioned on the front part of the waistband rather than along the sides, so as to improve user comfort.

U.S. Pat. No. 6,447,628 describes a method for producing resealable absorbent sanitary articles in which the closing elements of the waistbands are located on the front parts of the articles. This arrangement is obtained by making a continuous chain of blanks of absorbent sanitary articles which have front waist regions with a shorter length than the rear waist regions. In order to produce absorbent sanitary articles of this type with a Cross Direction production technique, it is necessary to remove longitudinal stretches of one of the two waistbands of the continuous composite tape.

U.S. Pat. No. 6,447,628 describes a method in which the removal of portions of one of the waistbands is performed before the longitudinal folding of the continuous composite tape.

The solution described in U.S. Pat. No. 6,447,628 is difficult to implement in practice because after removing portions of one of the longitudinal bands of the continuous composite tape it becomes very difficult to perform the longitudinal folding of the continuous composite tape with the necessary precision.

SUMMARY OF THE INVENTION

This aim of the present invention is to provide a method and an apparatus for producing absorbent sanitary articles wearable as pants having waistband sealing zones located on the front parts of the articles, which overcomes the problems of the prior art.

According to the present invention, that aim is achieved by a method and an apparatus having the features disclosed herein.

The claims are an integral part of the teaching supplied relative to the invention.

BRIEF DESCRIPTION OF THE DRAWINGS

The present invention will now be described in detail with reference to the accompanying drawings, given purely by way of non-limiting example, in which:

FIG. 1 is a schematic side view of an apparatus for producing absorbent sanitary articles according to the present invention.

FIG. 1A is a perspective view of an absorbent sanitary article wearable as pants having waistband sealing zones located on its front part.

FIG. 2 is a schematic view illustrating an embodiment of a method for producing absorbent sanitary articles of the type illustrated in FIG. 1A.

FIGS. 3A to 8A are schematic plan views illustrating in more detail various steps of the method of FIG. 2.

FIGS. 3B to 8B are schematic cross-section views corresponding to the steps of the process illustrated in FIGS. 3A to 8A, respectively.

Figure 3A:
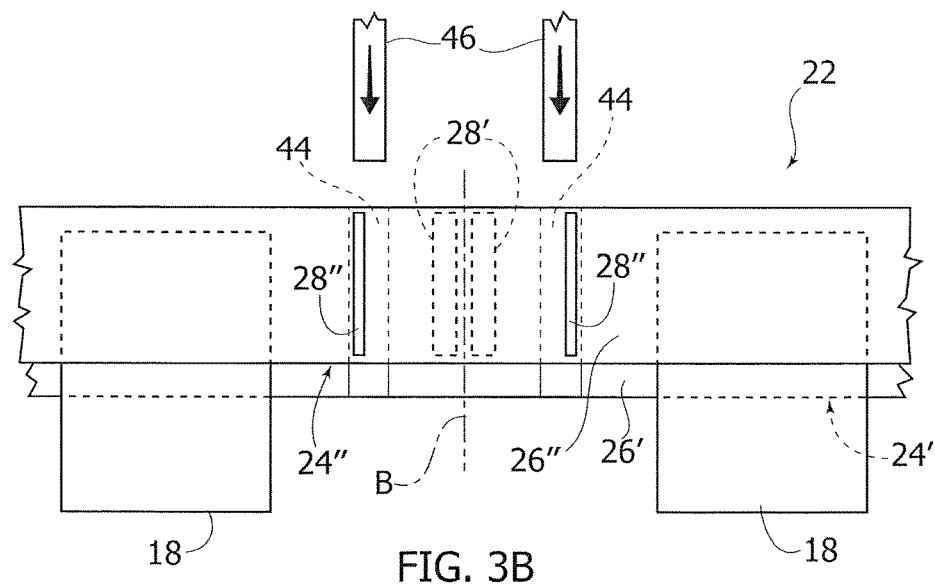

For clarity and simplicity of illustration the figures may not be shown with the same scale.

DETAILED DESCRIPTION

With reference to FIG. 1, the numeral 10 denotes an apparatus for producing absorbent sanitary articles wearable as pants, for example the so-called training pants.

In FIG. 1A the numeral 12 denotes an absorbent sanitary article which can be produced with the apparatus 10 of FIG. 1. The absorbent sanitary article 12 has a waistband 14 including a front elastic band 24" and a rear elastic band 24', which are joined together by closing elements 28', 28" located on the front part of the article 12. The absorbent sanitary article 12 comprises an absorbent core 18 folded into a U shape with the opposite ends fixed to the front waistband 24" and to the rear waistband 24'. The absorbent core 18 and the waistband 14 define leg openings 20. The length of the front waistband 24" is less than that of the rear waistband 24', meaning that the closing elements 28', 28" are located on the front part of the absorbent sanitary article 12 rather than on the sides. The closing elements 28', 28" may be replaced with welds in the case of permanently sealed absorbent sanitary articles.

Absorbent sanitary articles 12 of this type may have different configurations above all as regards the shape of the leg openings 20. In particular, the absorbent sanitary articles 12 may be produced starting from a single composite tape on which a series of through openings with a suitable contour is formed, each of which helps to define the outline of the leg opening 20 of two consecutive absorbent sanitary articles. Typically, the absorbent core 18 is located between two consecutive openings. Alternatively, the leg openings 20 may be obtained by arranging two elastic bands which are separate and parallel and are connected to each other by absorbent cores oriented orthogonally to the elastic bands and spaced apart from each other in a longitudinal direction.

Hereinafter in the description, without affecting its general nature, reference will be made to producing absorbent sanitary articles with elastic waistbands formed by two elastic webs which are separate and parallel, connected to each other by absorbent cores. However, it shall be understood that the method and the apparatus for producing absorbent sanitary articles which will be described below may also be used for producing absorbent sanitary articles obtained starting from a single composite tape in which through openings forming the leg openings are made, as for example described in U.S. Pat. No. 6,447,628.

With reference to FIGS. 1 and 2, the apparatus 10 processes a continuous composite tape 22 advancing in a machine direction MD. With reference to FIG. 2, the continuous composite tape 22 is formed by a continuous chain of blanks of absorbent sanitary articles, oriented with the respective longitudinal axes transversal with respect to the machine direction MD. The continuous composite tape 22 comprises a first continuous elastic band 24' and a second continuous elastic band 24", referred to for convenience with the same numerals of the corresponding rear elastic band and rear waistband, and front elastic band and front waistband in the absorbent sanitary article 12 of FIG. 1A, parallel to each other and parallel to the machine direction MD. The first and second continuous elastic bands 24', 24" are spaced apart from each other in a direction orthogonal to the machine direction MD. The continuous composite tape 22 comprises a plurality of absorbent cores 18 which extend between the first elastic band 24' and the second elastic band 24" orthogonally to the machine direction MD. The first elastic band 24' and the second elastic band 24" have, respectively, first connection zones 26' and second connection zones 26", intermediate between the absorbent cores 18. As already indicated, in an alternative embodiment the two continuous elastic bands 24', 24" may be incorporated in a single continuous composite tape which also incorporates the absorbent cores 18 and in which shaped through openings are formed which are located between the absorbent cores 18 and define leg openings.

With reference to FIG. 2, the continuous composite tape 22 has a longitudinal axis A which is intermediate between the outer edges of the first elastic band 24' and of the second elastic band 24". The absorbent cores 18 are spaced apart from each other along the longitudinal axis A with a constant pitch. On the continuous composite tape 22 it is possible to identify separation lines B orthogonal to the longitudinal axis A and intermediate between the absorbent cores 18. The separation lines 18 separate the blanks of absorbent sanitary articles from each other along the continuous composite tape 22.

The continuous composite tape 22 is initially in an outstretched configuration in which the first elastic band 24' and the second elastic band 24" are parallel and coplanar with each other.

In one embodiment, first closing elements 28' and second closing elements 28" may be applied on opposite surfaces of the connection zones 26', 26" of the elastic bands 24', 24". The closing elements 28', 28" are applied on the continuous composite tape 22 in the outstretched configuration. The closing elements 28', 28" are surface closing elements which can be connected to and separated from each other. The closing elements 28', 28" may be micro-hook and loop closing elements, commonly known under the brand name Velcro®. Alternatively, the closing elements 28', 28" may be closing elements with adhesive surfaces which can be separated from and reconnected to each other. The closing elements 28', 28" are applied and fixed on the surfaces of the elastic bands 24', 24" using techniques well-known in the sector of production of absorbent sanitary articles, usually by means of glue or welding. In the depiction in FIG. 2, the first closing elements 28' are applied on the upper surface of the first elastic band 24' (the surface towards the observer) and the second closing elements 28" are applied on the lower surface of the second elastic band 24" (the surface away from the observer).

The closing elements 28', 28" are applied in pairs on the respective connection zones 26', 26", with the closing elements 28', 28" of each pair arranged symmetrically relative to the respective separation lines B. The pairs of first closing elements 28' and the pairs of second closing elements 28" are arranged with a different relative distance along the longitudinal axis A. The first closing elements 28' of each connection zone 26' are very near to each other whilst the second closing elements 28" of each connection zone 26" are spaced apart from each other along the axis A by a substantial distance.

The closing elements 28', 28" serve to make openable and resealable absorbent sanitary articles. In the method according to the present invention the application of closing elements 28', 28" should be considered optional and may be omitted if the method is intended for producing permanently sealed absorbent sanitary articles.

The continuous composite tape 22 advancing in the machine direction MD in an outstretched condition (that is to say, with the first elastic band 24' and the second elastic band 24" coplanar with each other) is subjected to an operation of longitudinal folding around the axis A. After the folding around the longitudinal axis A, the second elastic band 24" overlaps the first elastic band 24'. After the folding operation the absorbent cores 18 are folded in a U shape and the second connection zones 26" of the second elastic band 24" are superimposed on the first connection zones 26' of the first elastic band 24'.

In the scheme of FIG. 1 the numeral 27 denotes a feeding device which advances the continuous composite tape 22 in the outstretched configuration in the machine direction MD. The numeral 29 is used to schematically indicate an applicator device for applying the closing elements 28', 28" on the opposite surfaces of the elastic bands 24', 24". Also, in FIG. 1 the numeral 30 denotes a longitudinal folding device which performs the longitudinal folding of the continuous composite tape 22 advancing in the machine direction MD. The feeding device 27, the applicator device 29 and the longitudinal folding device 30 are well known in the sector of the production of absorbent sanitary articles.

Downstream of the longitudinal folding device 30 the continuous composite tape 22 in the folded condition is fed onto the periphery of a rotary cutting unit 32 which is driven to rotate about its own axis C in phase with the continuous composite tape 22. The rotary cutting unit 32 performs on the continuous composite tape 22 operations of cutting, folding and, optionally, welding as described in detail below.

Figure 11:
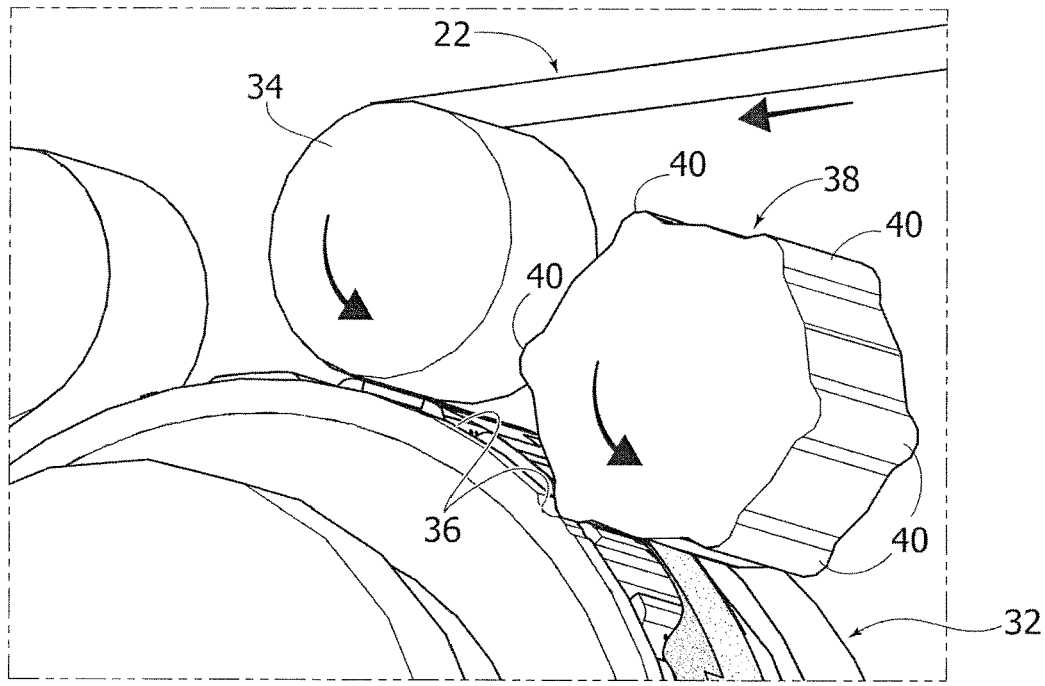
FIGS. 11 to 18 are perspective views illustrating details of various operating steps carried out on the cutting unit of FIG. 10.

With reference to FIGS. 1 and 11, the continuous composite tape 22 in the folded configuration is fed to the periphery of the rotary cutting unit 32 by an infeed roller 34. The composite tape 22 in the folded configuration is deposited on the rotary cutting unit 32 with the first elastic band 24' directly in contact with the outer surface of the rotary cutting unit 32 and with the second elastic band 24" folded on the first elastic band 24'. The outer surface of the rotary cutting unit 32 is provided with a plurality of recesses 36. The continuous composite tape 22 is advanced with predetermined phase relationship relative to the rotary cutting unit 32, in such a way that the connection zones 26', 26" which are superimposed on each other are positioned at the recesses 36. More precisely, each pair of connection zones 26', 26" is located at two adjacent recesses 36, which are spaced apart from each other in the circumferential direction. Each recess 36 is located at a respective second closing element 28".

With reference to FIG. 11, the connection zones 26', 26" which are superimposed on each other of the continuous composite tape 22 are pressed into the recesses 36 of the rotary cutting unit 32, for example by means of a wheel 38 whose outer surface is provided with projections 40 shaped to match the recesses 36.

Figure 3B:
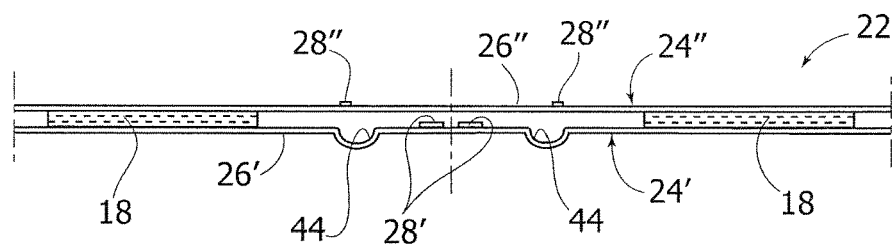
Figure 10:
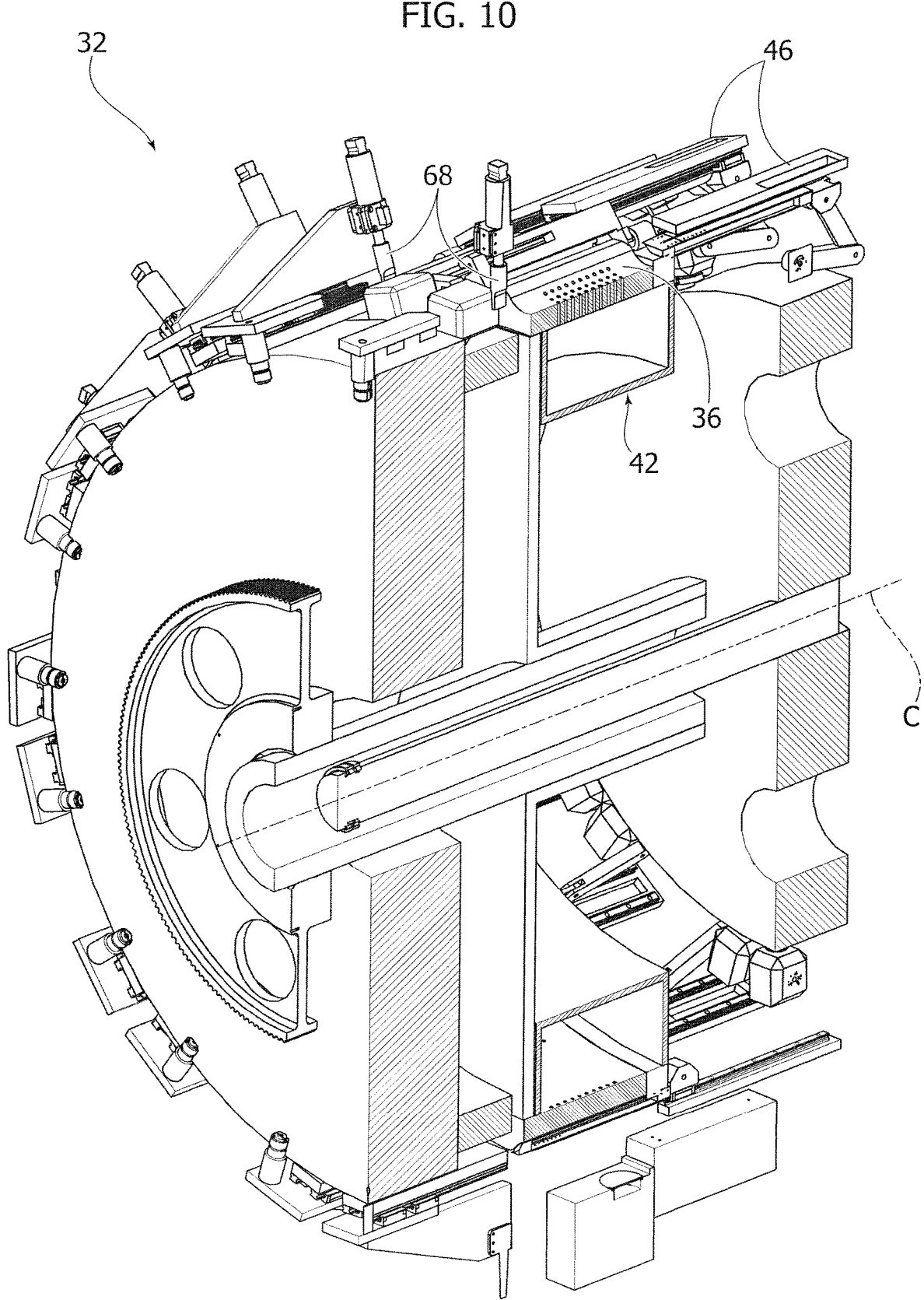
FIG. 10 is a perspective view partly in cross-section of a cutting unit of an apparatus for producing absorbent sanitary articles.
Figure 12:
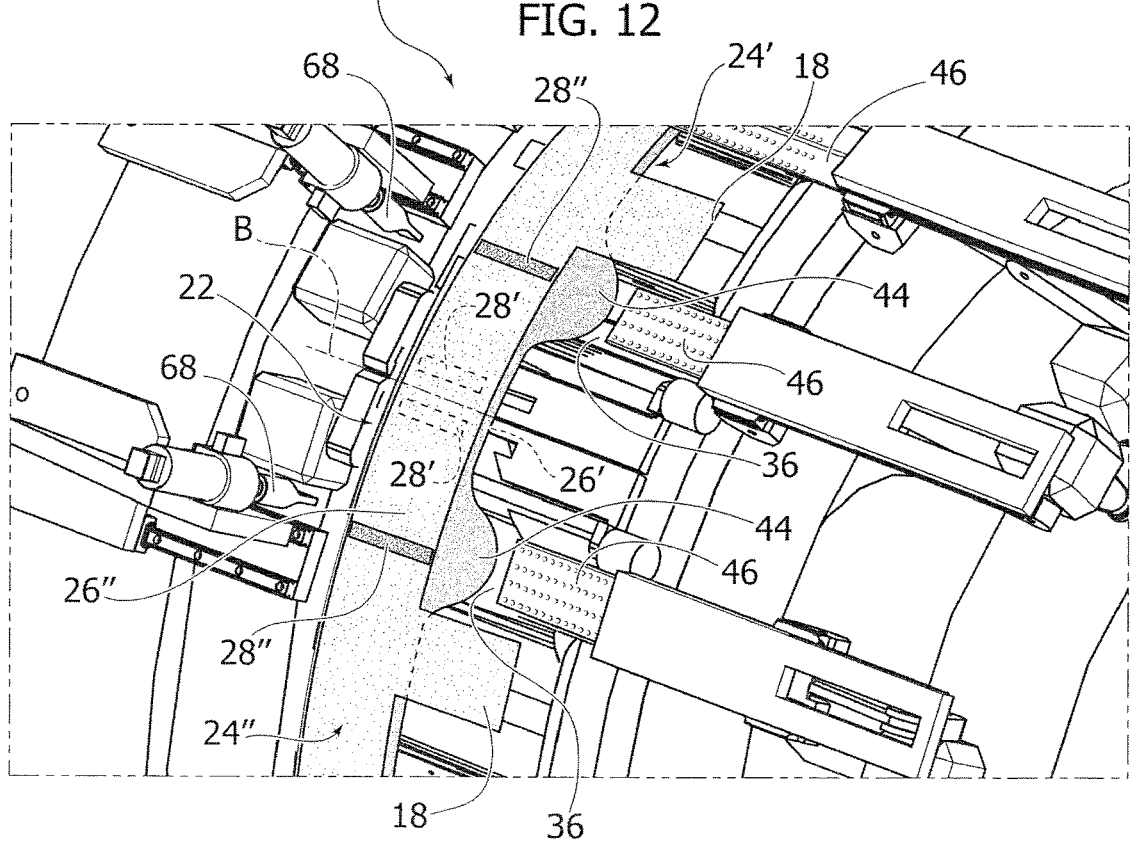

With reference to FIGS. 1 and 10, a stationary suction chamber 42 connected to a vacuum source is positioned inside the rotary cutting unit 32. The recesses 36 are provided with holes in communication with the suction chamber 42. The suction produced by the suction chamber 42 retains inside the recesses 36 corresponding portions of the first elastic band 24'. In contrast, the second elastic band 24" is not retained by the suction force, for example because the first elastic band 24', usually impermeable to air, prevents the suction action from reaching the second elastic band 24". Therefore, downstream of the wheel 38 portions of the first elastic band 24' are retained by suction in the respective recesses 36 whilst the second elastic band 24" returns to an outstretched position. In this way, at the recesses 36 empty spaces are formed, labelled 44 in FIG. 12, due to local detachment between the first elastic band 24' and the second elastic band 24". This condition is illustrated in FIGS. 3*a* and 3*b*. These figures show that the empty spaces 44 formed by the recesses 36 are located at the respective second closing elements 28".

Figure 4A:
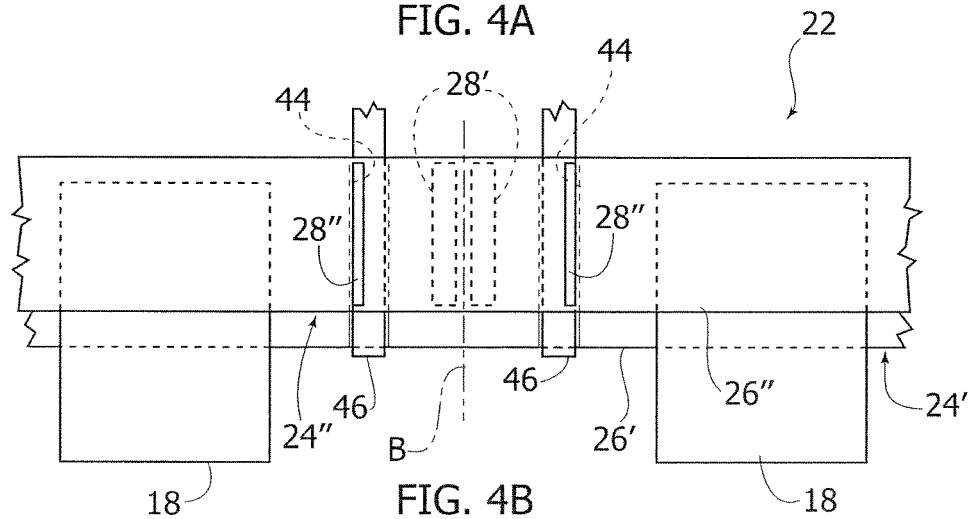
Figure 4B:
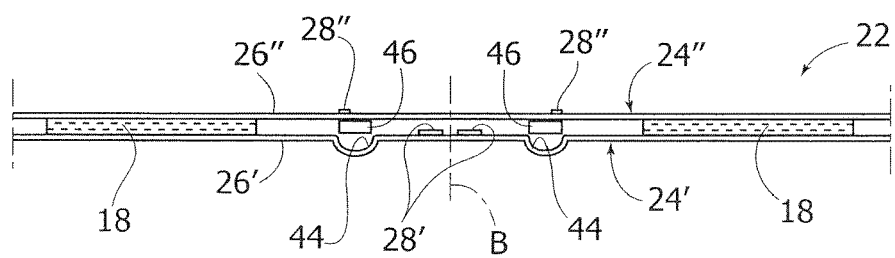
Figure 13:
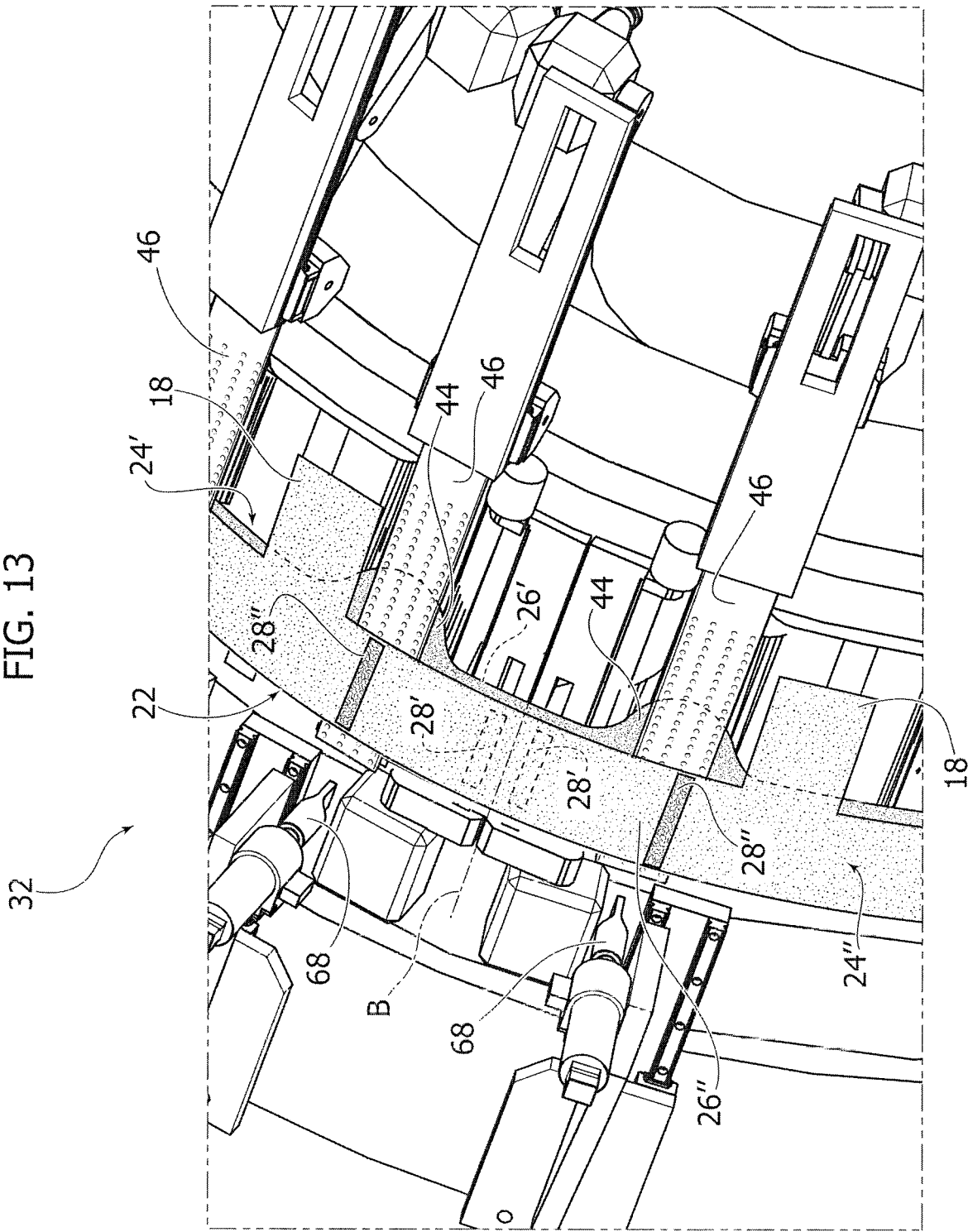

In a subsequent step illustrated in FIGS. 4A, 4B and 13, blade-shaped anvil elements 46 are inserted in respective empty spaces 44 between the first elastic band 24' and the second elastic band 24" and at the second closing elements 28". The anvil elements 46 are carried by the rotary cutting unit 32 and are moved between respective non-operating positions and operating positions along directions parallel to the axis of rotation C of the rotary cutting unit 32. The anvil elements 46 may be provided with holes connected to a suction source and located on the upper surfaces facing the second elastic band 24", in such a way as to retain by suction the portions of the second elastic band 24" facing the anvil elements 46.

Figure 5A:
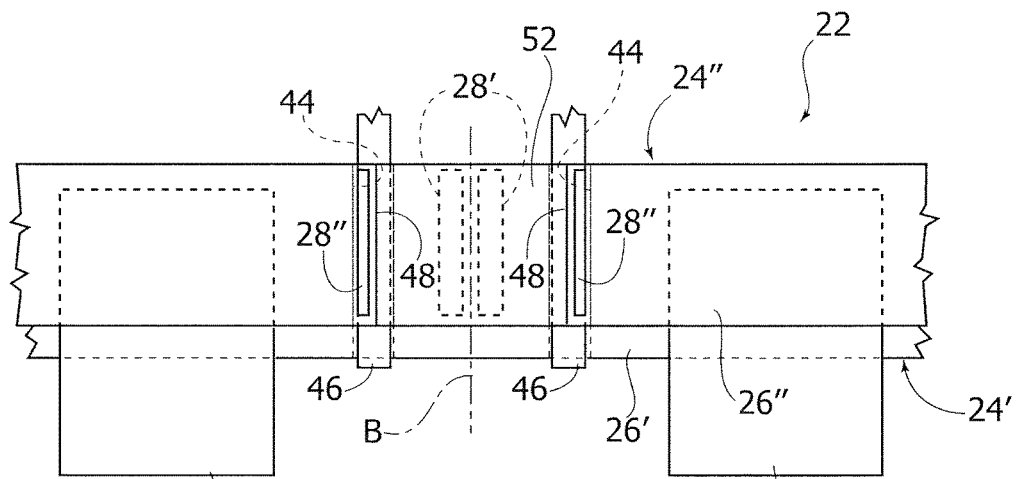
Figure 5B:
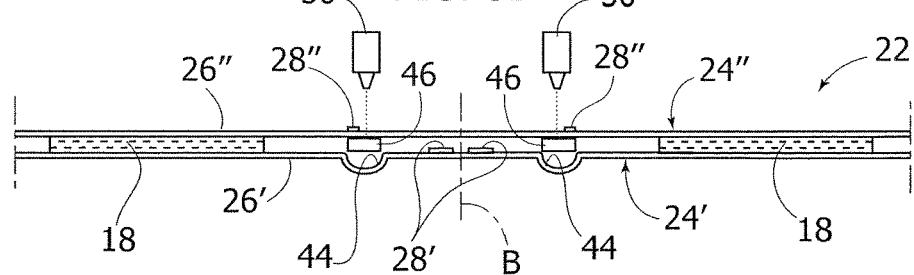
Figure 14:
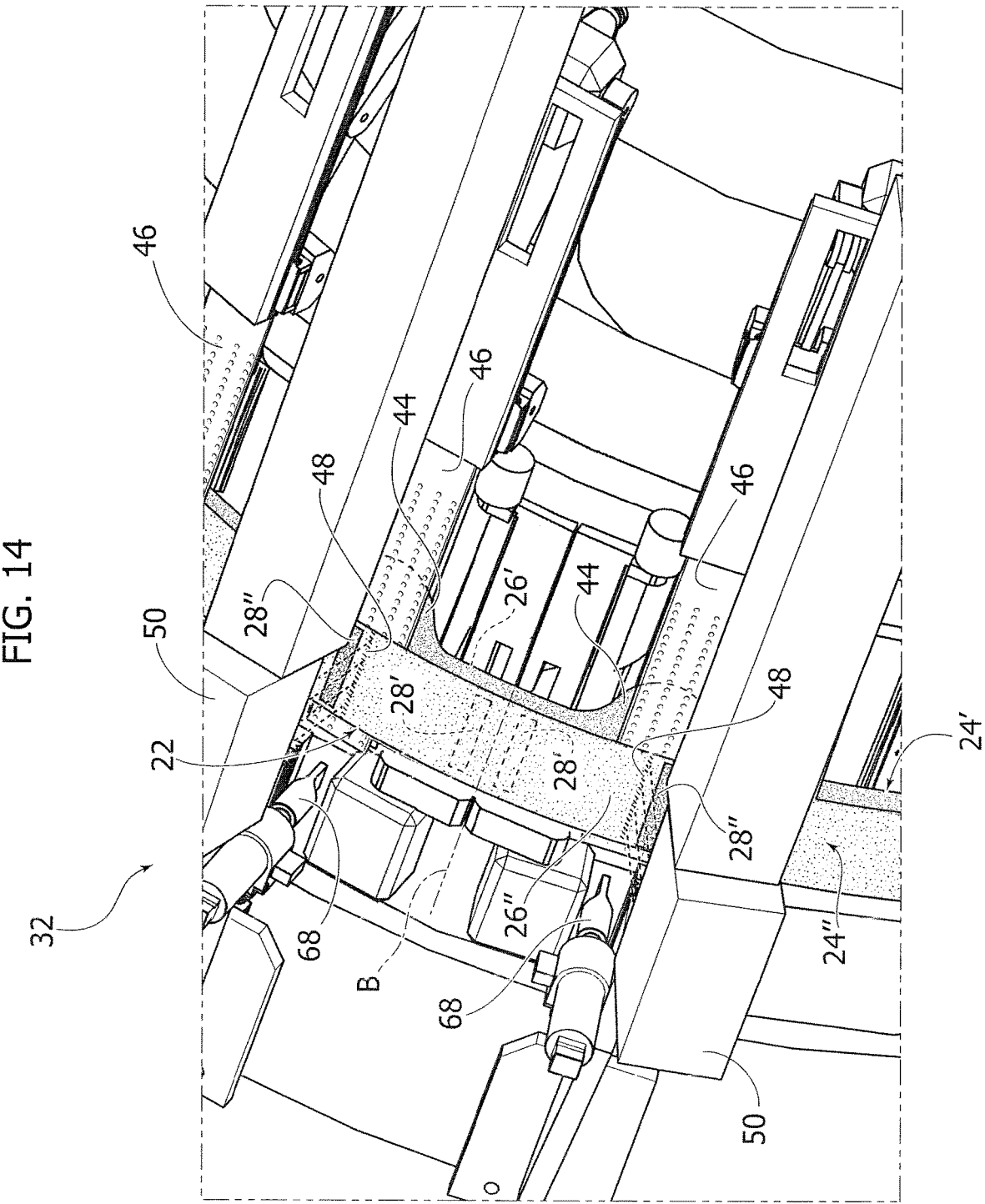
Figure 15:
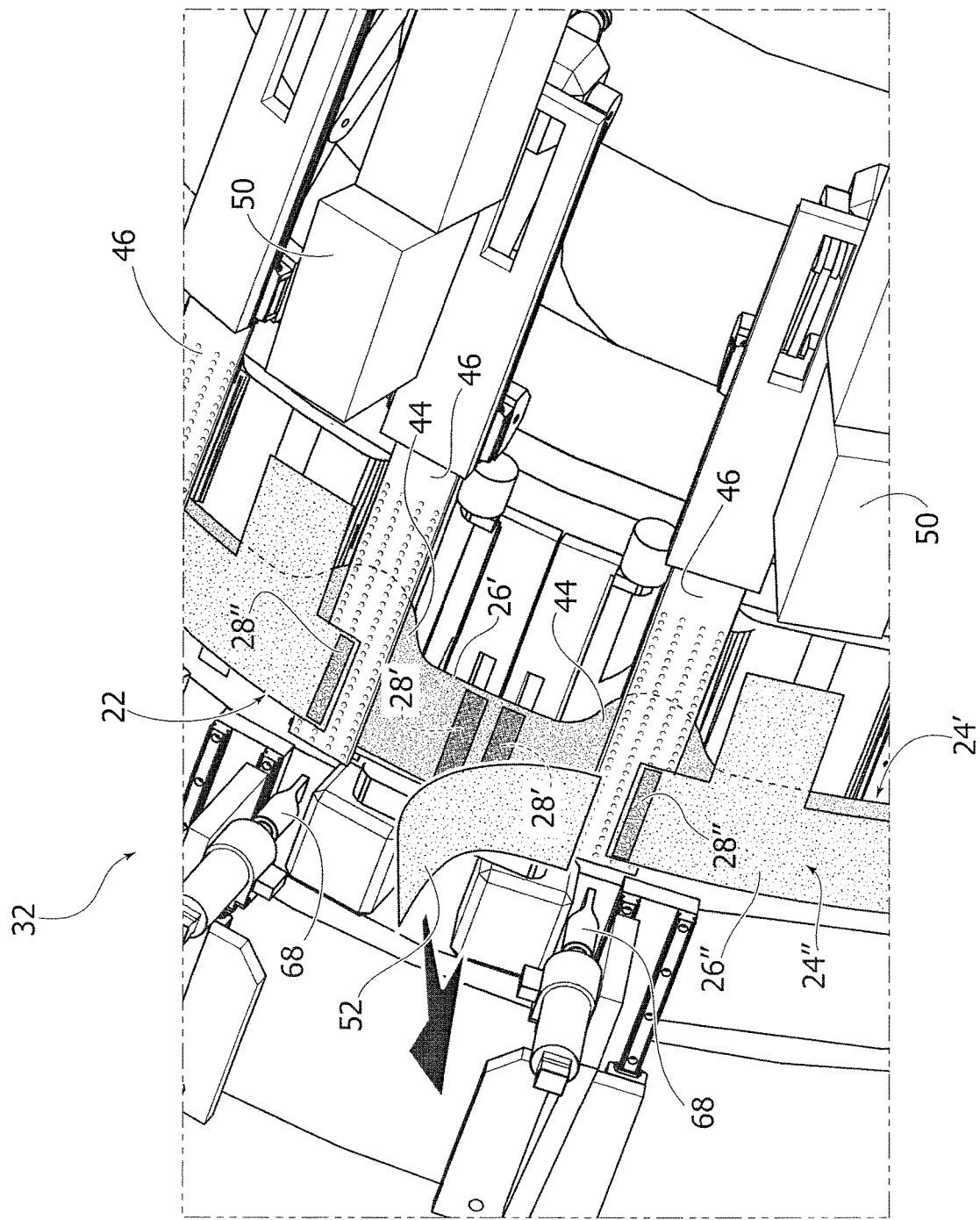

In a subsequent step illustrated in FIGS. 5A, 5B and 14 cuts 48 are made on the second elastic band 24" which in the embodiment described are made by means of a laser 50. The cuts 48 may also be made using other technologies, such as ultrasound, rotary blades, hot wire systems, etc. In the case of laser cutting, the cuts 48 are made on the anvil elements 46. The anvil elements 46 ensure that the laser beam only cuts the second elastic band 24". The first elastic band 24' is located below the anvil elements and is not affected by the laser beams which make the cuts 48. The cuts 48 completely cut the second elastic band 24" between two opposite lateral edges. The cuts 48, preferably orthogonal to the machine direction MD, may be adjacent to respective edges of the closing elements 28" towards the separation line B. With reference to FIG. 14, the laser cuts 48 are made using respective laser cutting heads 50 mounted in a fixed position on the rotary cutting unit 32. The laser cutting heads 50 can be moved along respective directions parallel to the axis of rotation of the rotary cutting unit 32 in order to make the cuts 48. The two cuts 48 form on each connection zone 26" a scrap portion 52 of the second elastic band 24", between the two resealable closing elements 28".

Figure 6A:
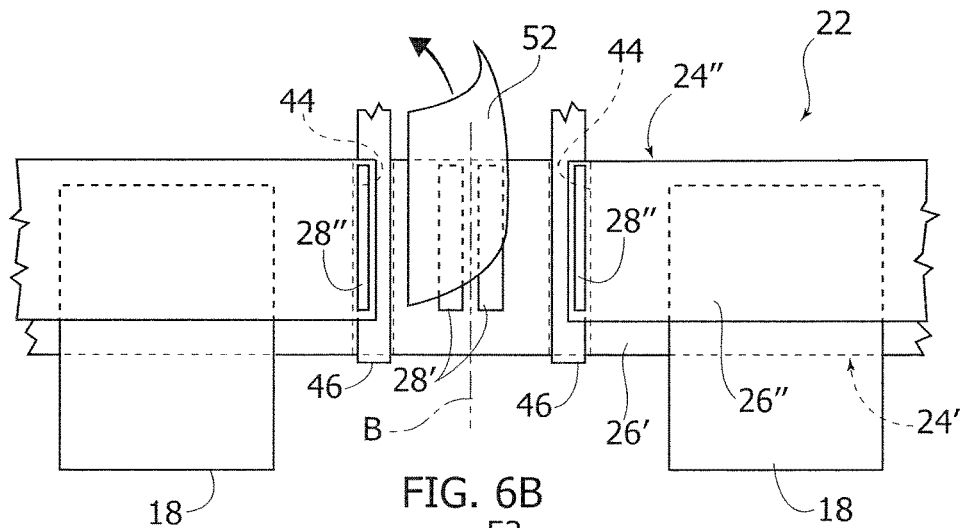
Figure 6B:
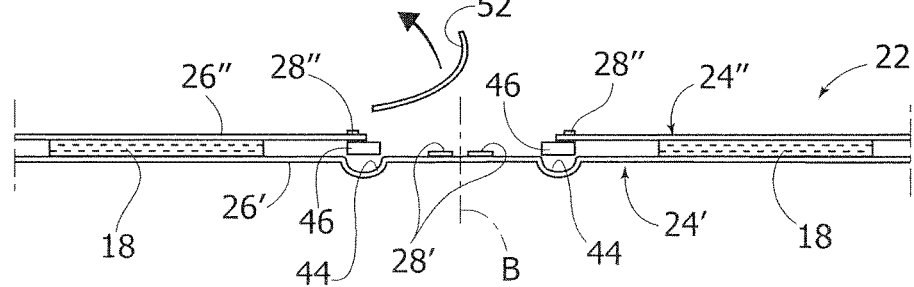
Figure 7A:
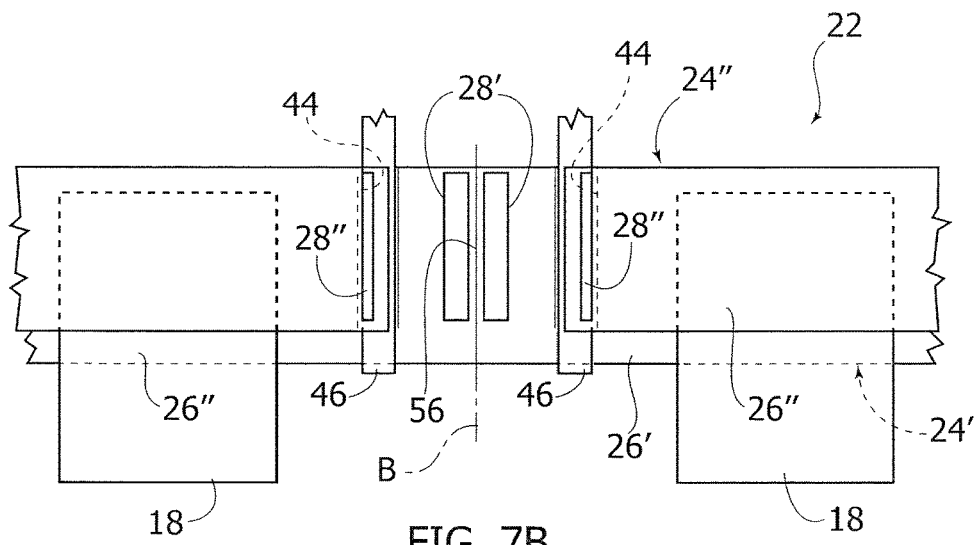
Figure 7B:
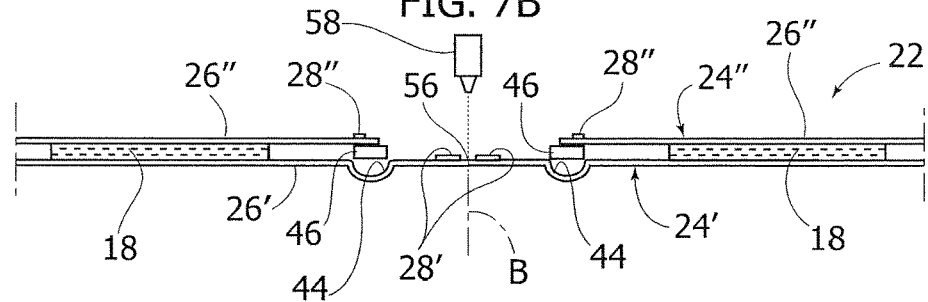
Figure 16:
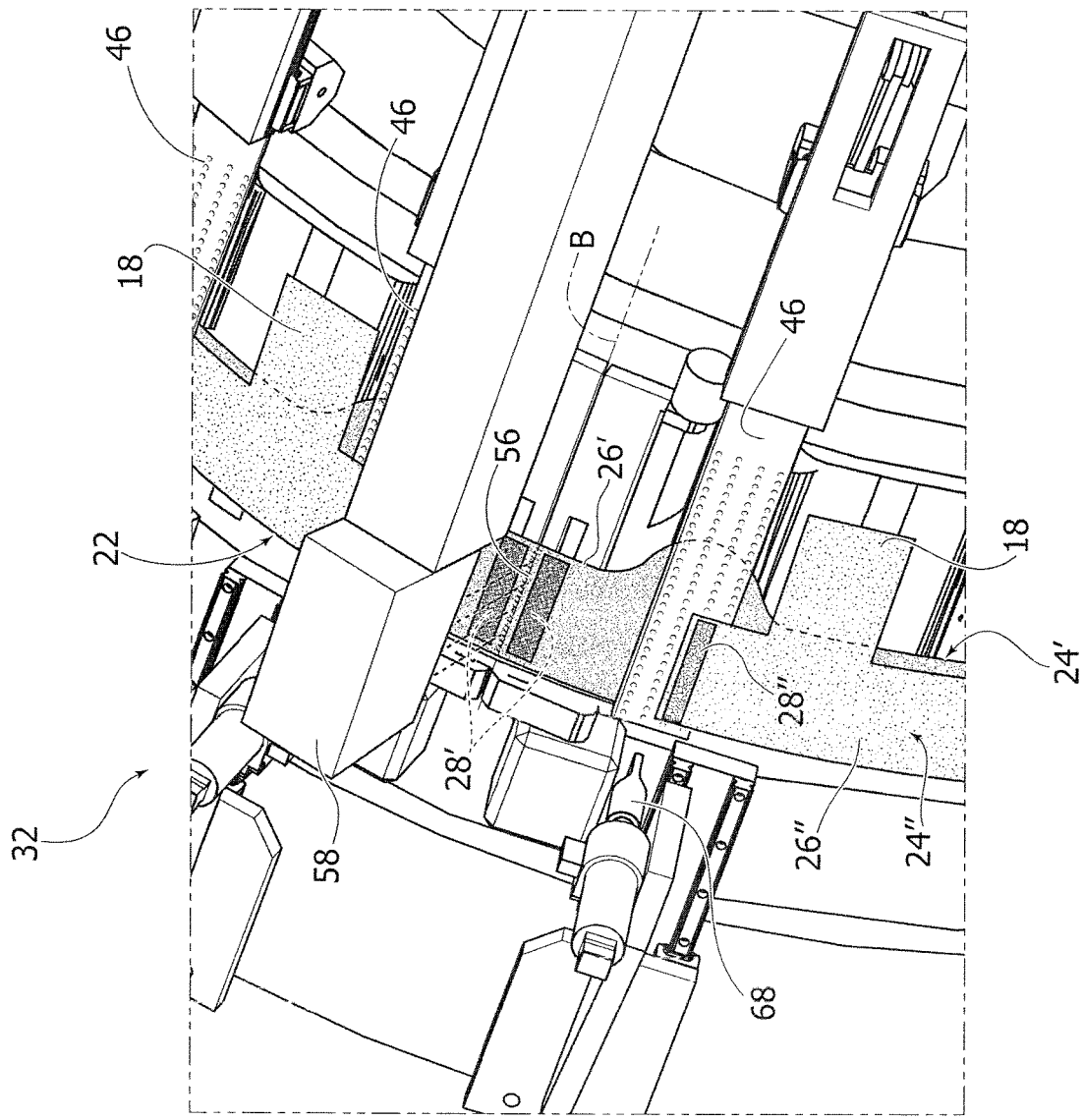

In each connection zone 26", the scrap portion 52 between the two cuts 48 is removed as schematically illustrated in FIGS. 6A, 6B e 15. Removal of the scrap portion 52 of the second elastic band 24" may be performed by means of a suction wheel labelled 54 in FIG. 1. After removal of a scrap portion 52 of the second elastic band 24", the corresponding connection zone 26' of the first elastic band 24' remains exposed on the surface of the rotary cutting unit 32. At this point, with reference to FIGS. 7A, 7B and 16, a second cut 56 is made on the first elastic band 24' between the two resealable closing elements 28' of each connection zone 26'. The second cut 56 extends from one edge to the other of the first elastic band 24' along the separation line B between two adjacent blanks of absorbent sanitary articles. The second cut 56 is made using a further laser cutting head 58, as illustrated in FIG. 16. The laser cutting head 58 is installed in a fixed radial position on the rotary cutting unit 32 and can be moved along a direction parallel to the axis of rotation C of the rotary cutting unit 32.

Figure 8A:
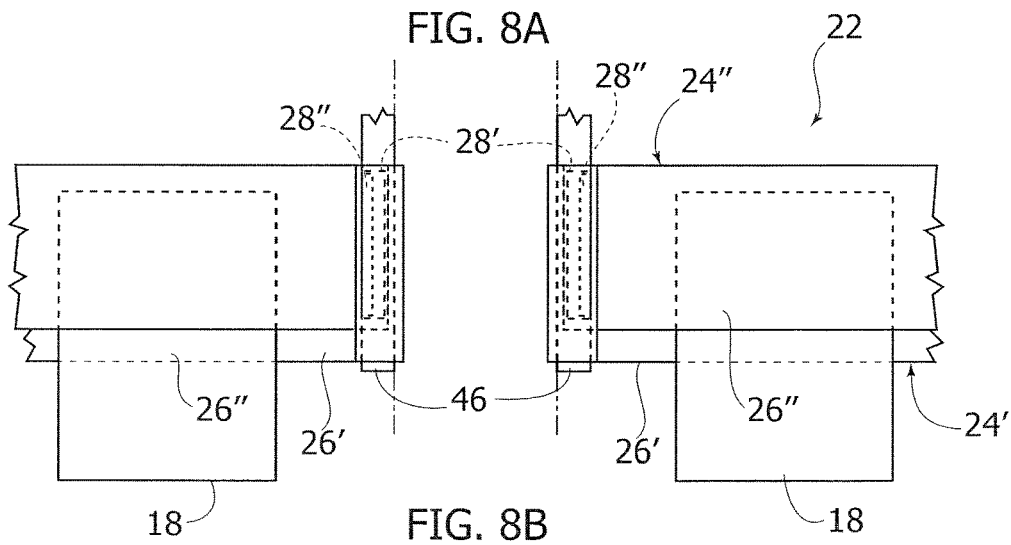
Figure 8B:
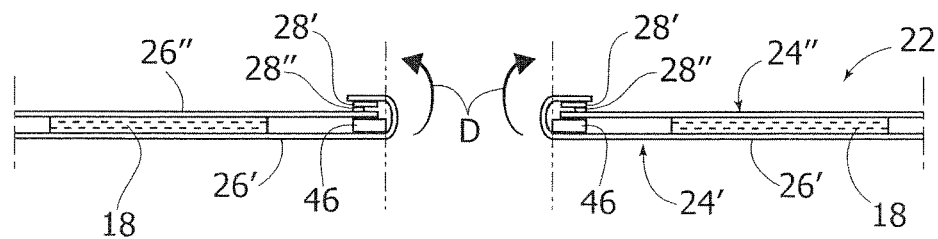
Figure 18:
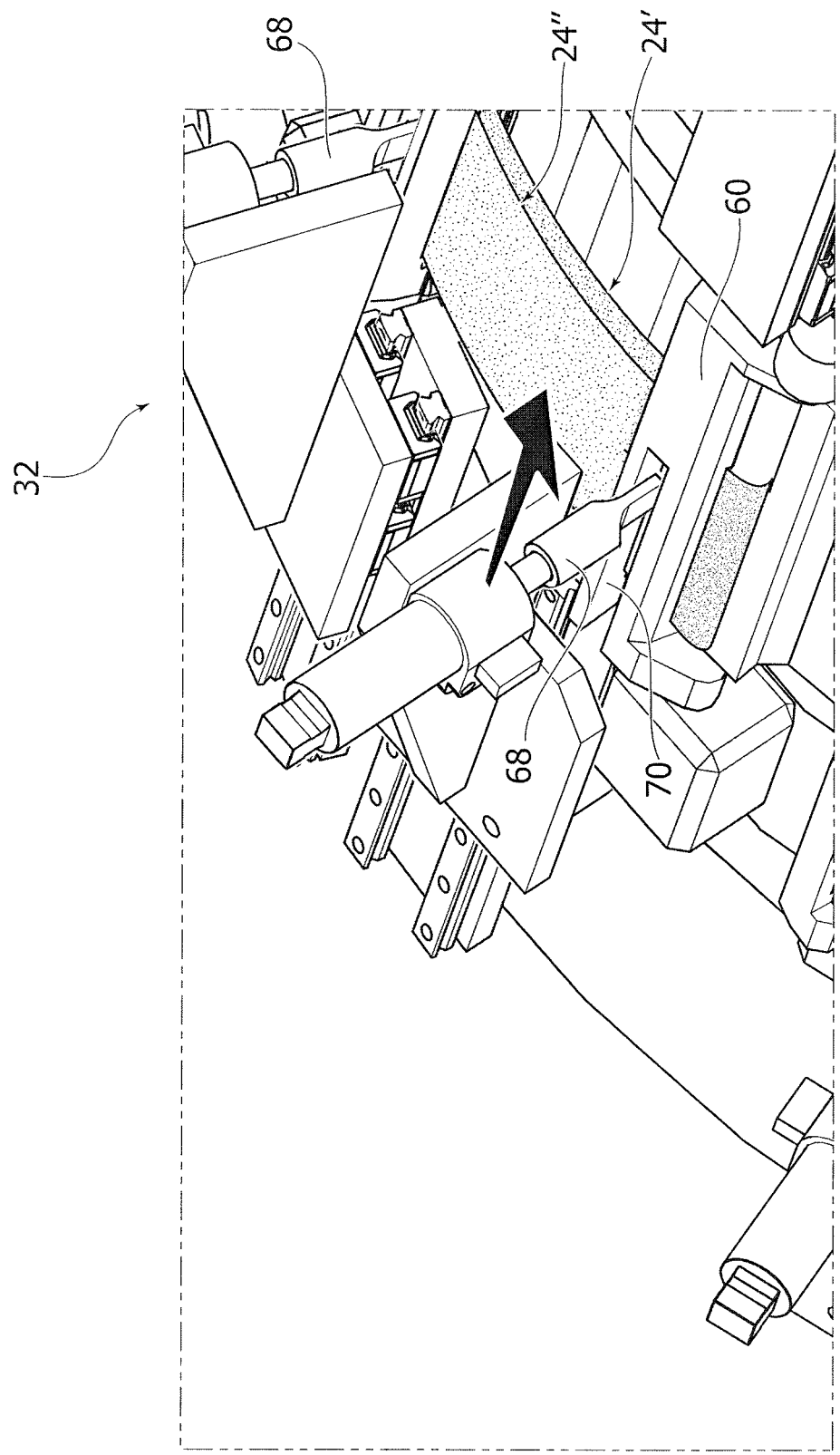

The second cuts 56 separate each connection zone 26'. The two parts of each connection zone 26' which are located on opposite sides of the cut 56 are then folded in opposite directions as illustrated in FIGS. 8A, 8B and 18. Each of the two portions of the first connection zone 26' are folded on corresponding portions of the second connection zone 26", in the directions indicated by the arrows D in FIG. 8B. After this folding, in each of the connection zones 26', 26" the closing elements 28' applied to the first elastic band 24' are connected to the corresponding complementary closing elements 28" which are fixed to the second elastic band 24".

Figure 17:
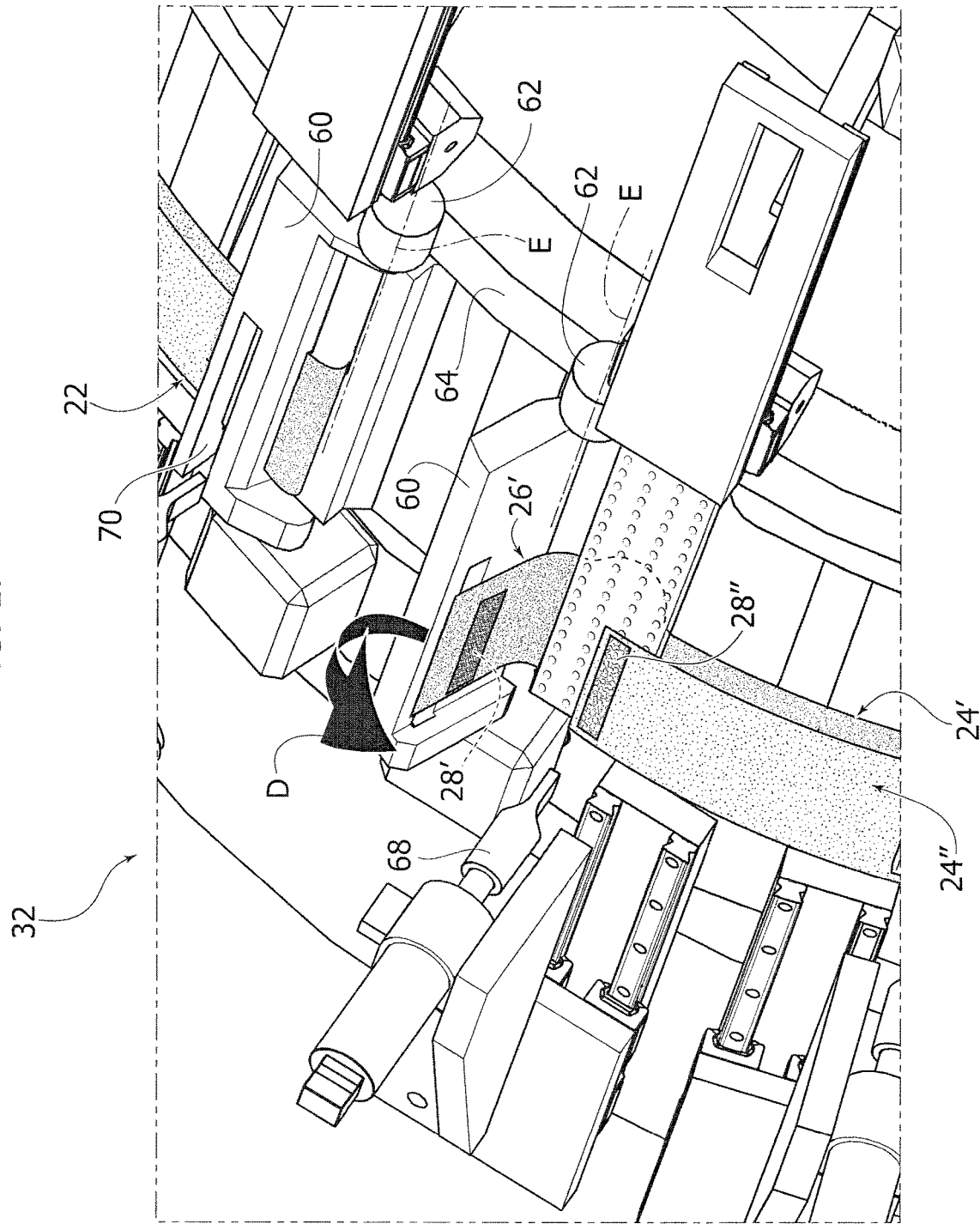

As illustrated in FIG. 17, the folding of the two portions of each connection zone 26' is performed by folding elements 60, which are carried by the rotary cutting unit 32 and rotatable relative to the rotary cutting unit 32 about respective axes E which are transversal to the machine direction. The oscillation of the folding elements 60 about the respective axes E may for example be controlled by cam followers 62 which are connected to the folding elements 60 and which operate in conjunction with a stationary cam 64.

After folding of the connection zones 26' of the first elastic band 24' on the connection zones 26" of the second elastic band 24" and connecting of the closing elements 28', 28" to each other, on the outer surface of the rotary cutting unit 32 a continuous chain of finished absorbent sanitary articles is formed, each of which is shaped as illustrated in FIG. 1A. The finished absorbent sanitary articles are detached from the rotary cutting unit 32 by means of an outfeed roller labelled 65 in FIG. 1.

Figure 9A:
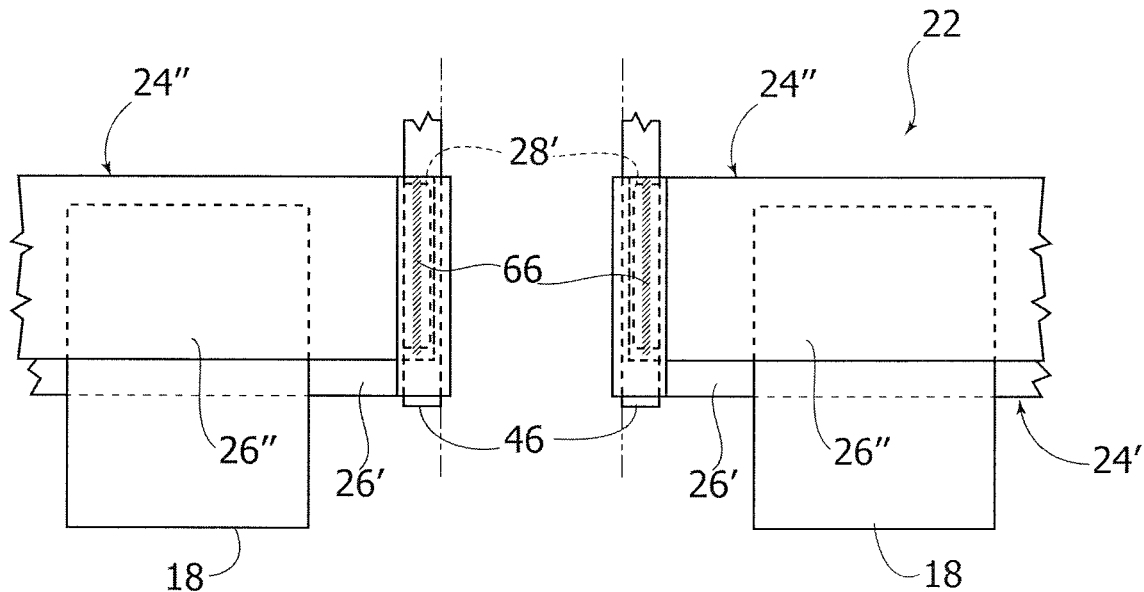
FIG. 9A is a plan view illustrating an alternative embodiment of the method for producing absorbent sanitary articles.
Figure 9B:
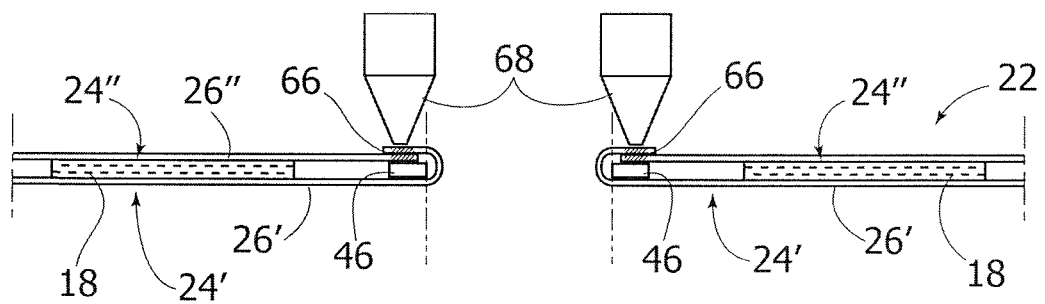
FIG. 9B is a schematic cross-section view corresponding to the step of FIG. 9A.

In an alternative embodiment of the present invention the resealable closing elements 28', 28" may be omitted. In this case the connection zones 26' of the first elastic band 24' are fixed by means of welding to the connection zone 26" of the second elastic band 24". This alternative embodiment is illustrated in FIGS. 9A, 9B and 18. In this alternative embodiment the method comprises all of the steps previously described with reference to FIGS. 3A to 8A, 3B to 8B and 11 to 17, the only difference being that the closing elements 28', 28" are not applied on the elastic bands 24' and 24". After folding of the connection zones 26' of the first elastic band 24' on the connection zones 26" of the second elastic band 24" transversal welds 66 are made which permanently join the two ends superimposed on each other of the connection zones 26', 26". The welds 66 may be ultrasonic welds made using ultrasonic welding heads 68 (FIG. 18) carried by the rotary cutting unit 32. The ultrasonic welding heads 68 may be moved in a direction parallel to the rotary cutting unit 32 for making the welds 66. The ultrasonic welds 66 may be made using the anvil elements 46 as counter-welding elements. The folding elements 60 hold the ends of the connection zones 26', 26" overlapping each other and may be provided with channels 70 through which to insert the respective ultrasonic welding head 68 for making the welds 66.

It shall be understood that removal of the scrap portions 52 from the second elastic bands 24" means that in the finished absorbent sanitary articles the front parts of the waistbands are shorter than the rear parts. The rear parts of the waistbands of the absorbent sanitary articles are folded around the user hip zones and are connected to the front parts of the waistbands along connection zones located on the front parts of the absorbent sanitary articles. Therefore, this avoids the presence of connection zones along the hips of the user.

One characteristic of the method and of the apparatus according to the invention is that removal of the scrap portions 52 is performed on the continuous composite tape 22 in the folded condition, that is to say, downstream of the step of longitudinal folding of the continuous composite tape 22. In this way, folding of the continuous composite tape 22 is performed when both of the elastic bands 24', 24" are continuous. The cuts which interrupt the continuity of the elastic bands 24', 24" are only made when the tape is already in a folded configuration. The fact that the cuts are made in the elastic bands 24', 24" on the composite tape 22 in the folded configuration guarantees greater precision of the folding step and improved finished product quality.

Naturally, without prejudice to the principle of the invention, the construction details and embodiments may widely vary compared with what is described and illustrated, without thereby departing from the scope of the invention as defined in the following claims.

The invention claimed is:

1. A method for producing absorbent sanitary articles, including:
    advancing in a machine direction a continuous composite tape in an outspread condition, formed by a continuous chain of blanks of absorbent sanitary articles oriented with the respective longitudinal axes transversal with respect to said machine direction, wherein said continuous composite tape comprises a first elastic band and a second elastic band, parallel to said machine direction, and a plurality of absorbent cores which extend between the first elastic band and the second elastic band orthogonally to the machine direction, wherein said first elastic band and said second elastic band have respectively first connection zones and second connection zones intermediate between said absorbent cores,
    folding said continuous composite tape around a longitudinal axis parallel to the machine direction and overlapping said second elastic band to said first elastic band, with the respective first and second connection zones superimposed on each other,
    advancing said folded continuous composite tape on a rotating cutting unit on which the following operations are carried out:
        carrying out on each of said second connection zones superimposed on respective first connection zones two first cuts spaced apart from each other,
        removing scrap portions of said second elastic band between said first cuts,
        carrying out on each of said first connection zones a second cut along a line intermediate between said first cuts; and
        folding in opposite directions portions of said first connection zone located on opposite sides of said second cut and overlapping end edges of said first connection zone to corresponding end edges of said second connection zone; and
    inserting a pair of anvil elements between the first and second elastic bands in each of said overlapped connection zones and cutting said second connection zones on said anvil elements.

2. A method according to claim 1, comprising applying closing elements on opposite surfaces of said first and second connection zones on said composite tape in an outstretched condition; and
    releasably connecting end edges of said first and second connection zones by means of said closing elements.

3. A method according to claim 1, comprising welding end edges superimposed on each other of said first and second connection zones.

4. A method according to claim 1, comprising:
pushing portions of said first and second connection zones superimposed on each other within corresponding recesses;
retaining within said recesses portions of the first connection zones and releasing portions of the second connection zones thus forming empty spaces between the first and second connection zones; and
inserting said anvil elements into respective empty spaces.

5. A method according to claim 1, comprising carrying out welds between said end edges of said first and second connection zones superimposed on each other with said anvil elements acting as counter-welding elements.

6. A method according to claim 1, wherein said operations of cutting said first and second connection zones are carried out by laser cutting heads.

7. An apparatus for producing absorbent sanitary articles, comprising:
a feeding device for advancing in a machine direction a continuous composite tape formed by a continuous chain of blanks of sanitary absorbent articles oriented with the respective longitudinal axes transverse to said machine direction, wherein said continuous composite tape comprises a first elastic band and a second elastic band, parallel to said machine direction and spaced apart in a direction orthogonal to the machine direction, and a plurality of absorbent cores extending between the first elastic band and the second elastic band orthogonally to the machine direction, wherein said first elastic band and said second elastic band have, respectively, first connection zones and second connection zones intermediate between said absorbent cores,
a longitudinal folding device for folding said continuous composite tape about a longitudinal axis parallel to the machine direction and for superimposing said second elastic band to said first elastic band, with the respective first and second connection zones superimposed on each other,
a rotary cutting unit located downstream of said longitudinal folding device and comprising:
first cutting heads for cutting each of said second connection zones of said second elastic band forming in each of the second connection zones two first cuts spaced apart from each other;
a scrap removal element for removing scrap portions of said second elastic band between said first cuts;
a second cutting head for making a second cut on each of said first connection zones in an intermediate position between said first cuts;
at least one pair of folding elements rotatable about respective transversal axes to fold transversely in opposite directions to each other portions of each of said first connection zones located on opposite sides of said second cut and overlapping end edges of the first connection zone to corresponding end edges of the second connection zone; and
a plurality of anvil elements which can be inserted between said first and second connection zones.

8. An apparatus according to claim 7, comprising an application unit for applying resealable closure elements on opposite surfaces of said first and second connection zones in said continuous composite tape in an overstretched condition.

9. An apparatus according to claim 7, wherein said rotary cutting unit comprises a plurality of welding heads for welding said end edges superimposed on each other of said first and second connection zones.

10. An apparatus according to claim 7, wherein said rotary cutting unit comprises a wheel having a plurality of projections able to push portions of said first and second connection zones within respective recesses, a suction chamber for retaining by suction portions of said first connection zones into said recesses and releasing the second connection zones so as to form empty spaces between said first and second connection zones within which said anvil elements are inserted.

11. An apparatus according to claim 7, wherein said anvil elements act as counter-welding elements for welding heads.

12. An apparatus according to claim 7, wherein said first and second cutting heads are laser cutting heads.

* * * * *